(12) United States Patent
Pedretti et al.

(10) Patent No.: US 8,580,267 B2
(45) Date of Patent: Nov. 12, 2013

(54) IMMUNOCYTOKINES FOR TUMOUR THERAPY WITH CHEMOTHERAPEUTIC AGENTS

(75) Inventors: Marta Pedretti, Zurich (CH); Dario Neri, Buchs (CH)

(73) Assignee: Philogen S.p.A., Siena (IT)

( * ) Notice: Subject to any disclaimer, the term of this patent is extended or adjusted under 35 U.S.C. 154(b) by 0 days.

(21) Appl. No.: 13/139,655

(22) PCT Filed: Dec. 14, 2009

(86) PCT No.: PCT/EP2009/008920
§ 371 (c)(1),
(2), (4) Date: Jun. 14, 2011

(87) PCT Pub. No.: WO2010/078916
PCT Pub. Date: Jul. 15, 2010

(65) Prior Publication Data
US 2011/0250170 A1    Oct. 13, 2011

Related U.S. Application Data

(60) Provisional application No. 61/139,484, filed on Dec. 19, 2008.

(51) Int. Cl.
*A61K 39/395* (2006.01)
*A61K 38/20* (2006.01)
*A01N 43/713* (2006.01)

(52) U.S. Cl.
USPC .......... 424/178.1; 424/85.2; 514/183

(58) Field of Classification Search
None
See application file for complete search history.

(56) References Cited

FOREIGN PATENT DOCUMENTS

| WO | 02/059264 | 8/2002 |
|----|-----------|--------|
| WO | 03/093478 | 11/2003 |
| WO | 2004/002528 | 1/2004 |
| WO | 2006/026020 | 3/2006 |
| WO | 2006/050834 | 5/2006 |
| WO | 2007/128563 | 11/2007 |

OTHER PUBLICATIONS

Paul, William, Fundamental Immunology, 3rd Edition, Raven Press, New York, 1993, pp. 292-295.*
Vajdos et al., Comprehensive functional maps of the antigen-binding site of an anti-ErbB2 antibody obtained with shotgun scanning mutagenesis. J. Mol. Biol. 320:415-428, 2002.*
Bartolomei, M., et al. "Combined treatment of glioblastoma patients with locoregional pre-targeted 90Y-biotin radioimmunotherapy and temozolomide." Q J Nucl Med Mol Imaging. Sep. 2004;48(3):220-8.
Marlind, J., et al. "Antibody-mediated delivery of interleukin-2 to the stroma of breast cancer strongly enhances the potency of chemotherapy." Clin Cancer Res. Oct. 15, 2008;14(20):6515-24.
Brack, S.S., et al. "Tumor-targeting properties of novel antibodies specific to the large isoform of tenascin-C." Clin Cancer Res. May 15, 2006;12(10):3200-8.
Leins, A., et al. "Expression of tenascin-C in various human brain tumors and its relevance for survival in patients with astrocytoma." Cancer. Dec. 1, 2003;98(11):2430-9.
Ebbinghaus, C., et al. "Engineered vascular-targeting antibody-interferon-gamma fusion protein for cancer therapy." Int J Cancer. Aug. 20, 2005;116(2):304-13.

* cited by examiner

*Primary Examiner* — Ruixiang Li
(74) *Attorney, Agent, or Firm* — Dann, Dorfman, Herrell & Skillman; Kathleen D. Rigaut

(57) ABSTRACT

Immunocytokine comprising cytokine, e.g. interleukin 2 (IL-2), conjugated to antibody against tumour neovasculature antigen, e.g. tenascin-C, for use in combination therapy with chemotherapeutic agent such as temozolomide. Use of immunocytokine and chemotherapy for treatment of tumours e.g. glioblastoma and other cancers.

12 Claims, 6 Drawing Sheets

IMMUNOCYTOKINES FOR TUMOUR THERAPY WITH CHEMOTHERAPEUTIC AGENTS

This is a national stage application of PCT/EP2009/008920 filed on Dec. 14, 2009 which claims priority to U.S. Provisional patent application No. 61/139,484, filed on Dec. 19, 2008. The entire disclosure of each of the foregoing applications is incorporated by reference herein.

This invention relates to the treatment of tumours and cancer using a combination of chemotherapeutic agents and immunocytokines.

Conventional cytotoxic therapies of cancer often do not discriminate between tumour and normal tissues. To achieve therapeutically relevant concentrations in the tumour mass, large drug doses have to be administered to the patient, leading to a poor therapeutic index and unacceptable toxicities to healthy tissues [1]. The selective delivery of therapeutic agents to the tumour site using antibodies directed against tumour-associated antigens is a strategy to overcome the disadvantages of conventional cancer therapies [2, 3, 4]. Antigens that are expressed around the tumour neovasculature are especially attractive targets for antibody-based pharmacodelivery applications due to their inherent accessibility for blood-borne agents and to the fact that angiogenesis is a characteristic feature of virtually all aggressive solid tumours [5, 6, 7].

Tenascin-C is a large hexameric glycoprotein of the extracellular matrix which modulates cellular adhesion. It is involved in processes such as cell proliferation and cell migration and is associated with changes in tissue architecture as occurring during morphogenesis and embryogenesis as well as under tumourigenesis or angiogenesis.

A strong over-expression of the large isoform of tenascin-C has been reported for a number of tumours, and monoclonal antibodies specific for domains A1 and D, respectively, have been extensively characterised in the clinic [8, 9, 10, 11, 12]. Human monoclonal antibody fragments specific to tenascin-C are described in WO2006/050834 and shown to bind preferentially to tumour tissue relative to normal tissue. These antibodies are useful, for example, in delivering toxins, such as cytokines, specifically to tumour cells.

Delivery of bioactive agents to the subendothelial extracellular matrix has been demonstrated using derivatives of monoclonal antibodies specific to splice isoforms of fibronectin or of tenascin-C [5, 13, 14, 15, 16, 17, 18, 19, 20]. In particular, promising results obtained with derivatives of the human monoclonal antibodies L19 (specific to the alternatively spliced ED-B domain of fibronectin) and F16 (specific to the extra-domain A1 of tenascin-C) have led to the clinical development of five immunocytokines and radioimmunoconjugates, based on these antibodies [7, 13, 14, 15, 16, 21, 22]. F16 is also known as 4A1-F16.

L19 specifically binds the ED-B domain of fibronectin isoform B-FN, which is one of the best known markers of angiogenesis (U.S. Ser. No. 10/382,107, WO01/62298). ED-B is an extra domain of 91 amino acids found in the B-FN isoform and is identical in mouse, rat, rabbit, dog and man. B-FN accumulates around neovascular structures in aggressive tumours and other tissues undergoing angiogenesis, such as the endometrium in the proliferative phase and some ocular structures in pathological conditions, but is otherwise undetectable in normal adult tissues (19, 23, 24). ScFv(L19) has been shown to be capable of selective tumour targeting in patients with cancer [16]. Use of immunocytokines comprising L19 conjugated with IL-12 is described in WO2006/119897.

F16 and F16-IL2 have been shown to intensely stain aggressive cancer types and to preferentially accumulate at the tumour site following intravenous administration [22, 25]. Following observation of its excellent safety profile observed in cynomolgus monkeys, F16-IL2 is currently being studied in two phase Ib clinical trials in combination with doxorubicin or with paclitaxel in patients with metastatic cancer.

Central nervous system tumours rank first among neoplasia types for the average years of life lost [26]. Approximately 13,000 deaths and 18,000 new cases of central nervous system tumours occur annually in the US [27]. Mortality rates are generally similar to incidence rates in most geographical areas [28].

The standard of care for patients with glioblastoma includes surgery, radiotherapy and/or temozolomide-based pharmacotherapy. Nevertheless, the prognosis of glioblastoma continues to be dismal, in spite of progress made in the molecular characterisation of the most frequent genetic alterations found in this disease.

Microvascular proliferation is a characteristic feature of glioblastoma [35]. A striking over-expression of the EDB domain of fibronectin in high-grade astrocytomas has been unequivocally established [29; 30] and the monoclonal antibody L19 has been shown to target glioblastoma in patients [31]. Furthermore, radiolabelled preparations of monoclonal antibodies specific to the A1 or to the D domain of tenascin-C have been investigated for the radioimmunotherapy of patients with glioblastoma [32].

Bartolomei et al. [33] described treatment of glioblastoma patients with radioimmunotherapy, using biotinylated anti-tenascin murine monoclonal antibody, avidin and $^{90}$Y-biotin, in combination with temozolomide. Overall survival and progression free survival of patients receiving the combined treatment were observed to be higher compared with patients who received radioimmunotherapy without temozolomide.

The inventors have observed that the combination of an alkylating agent with an antibody-IL2 conjugate targeted to a tumour-associated antigen of the tumour neovasculature exhibited more effective therapeutic action against the tumour compared with the use of the alkylating agent or the conjugate alone.

F16-IL2 is shown herein to potentiate the therapeutic action of the alkylating agent temozolomide in mice models of human glioblastoma. A synergistic effect was observed for the combination of temozolomide and F16-IL2, which produced an anti-tumour effect much greater than would have been expected based on the effects of F16-IL2 or temozolomide alone. Subcutaneous U87 glioblastomas were completely eradicated in nude mice using the combination treatment, compared with only a minor retardation of tumour growth observed for F16-IL2 treatment alone and a recurrence of tumour growth following regression in mice treated with temozolomide alone.

Aspects of the first development of the invention are as follows.

Accordingly, a first development of the invention relates to the combined use of a chemotherapeutic alkylating agent and an immunocytokine for treating a tumour, where the immunocytokine comprises a cytokine (e.g. an interleukin such as IL2) conjugated with an antibody molecule, wherein the antibody molecule binds a target antigen, e.g. tumour-associated antigen and/or antigen of the tumour neovasculature.

A first aspect of the invention is a method of treating a tumour in an individual, comprising administering a chemotherapeutic agent and an immunocytokine to the individual, wherein the chemotherapeutic agent is an alkylating agent and wherein the immunocytokine comprises a cytokine conjugated to an antibody molecule that binds the target antigen.

A second aspect of the invention is use of a chemotherapeutic agent and an immunocytokine for the manufacture of a medicament for treatment of a tumour in an individual, wherein the chemotherapeutic agent is an alkylating agent and wherein the immunocytokine comprises a cytokine conjugated to an antibody molecule that binds the target antigen.

A third aspect of the invention is use of an immunocytokine for the manufacture of a medicament for treatment of a tumour in an individual, wherein the treatment comprises administering the immunocytokine and a chemotherapeutic agent to the individual, wherein the chemotherapeutic agent is an alkylating agent and wherein the immunocytokine comprises a cytokine conjugated to an antibody molecule that binds the target antigen.

A fourth aspect of the invention is use of a chemotherapeutic agent for the manufacture of a medicament for the treatment of a tumour in an individual, wherein the treatment comprises administering the chemotherapeutic agent and an immunocytokine to the individual, wherein the chemotherapeutic agent is an alkylating agent and wherein the immunocytokine comprises a cytokine conjugated to an antibody molecule that binds the target antigen.

A fifth aspect of the invention is an immunocytokine for use in treatment of a tumour in an individual, wherein the treatment comprises administering the immunocytokine and a chemotherapeutic agent to the individual, wherein the chemotherapeutic agent is an alkylating agent and wherein the immunocytokine comprises a cytokine conjugated to an antibody molecule that binds the target antigen.

A sixth aspect of the invention is a chemotherapeutic agent for use in treatment of a tumour in an individual, wherein the treatment comprises administering the chemotherapeutic agent and an immunocytokine to the individual, wherein the chemotherapeutic agent is an alkylating agent and wherein the immunocytokine comprises a cytokine conjugated to an antibody molecule that binds the target antigen.

A seventh aspect of the invention is a medicament comprising an immunocytokine and a chemotherapeutic agent, for use in treatment of a tumour in an individual, wherein the treatment comprises administering the medicament to the individual, wherein the chemotherapeutic agent is an alkylating agent and wherein the immunocytokine comprises a cytokine conjugated to an antibody molecule that binds the target antigen.

A second development of the invention relates to treatment of glioma using an immunocytokine, wherein the immunocytokine comprises a cytokine conjugated to an antibody molecule that binds a target antigen, e.g. tumour-associated antigen and/or antigen of the tumour neovasculature. The glioma may be glioblastoma.

As disclosed here, the inventors have discovered that a combination of a chemotherapeutic agent with an antibody-cytokine conjugate exhibits more effective therapeutic action against glioma compared with the use of the chemotherapeutic agent or the conjugate alone. By using a therapeutic regimen of combined administration of an immunocytokine with chemotherapy, the therapeutic activity of the immunocytokine and chemotherapeutic agent can be significantly increased. These findings are of particular value for therapy of glioblastoma, which is a devastating disease with very poor prognosis, and for which there is currently no definitive cure.

Aspects of the second development of the invention are as follows.

A first aspect is a method of treating glioma in an individual, comprising administering a chemotherapeutic agent and an immunocytokine to the individual, wherein the immunocytokine comprises a cytokine conjugated to an antibody molecule that binds the target antigen.

A second aspect is use of a chemotherapeutic agent and an immunocytokine for the manufacture of a medicament for treatment of glioma in an individual, wherein the immunocytokine comprises a cytokine conjugated to an antibody molecule that binds the target antigen.

A third aspect is use of an immunocytokine for the manufacture of a medicament for treatment of glioma in an individual, wherein the treatment comprises administering the immunocytokine and a chemotherapeutic agent to the individual, and wherein the immunocytokine comprises a cytokine conjugated to an antibody molecule that binds the target antigen.

A fourth aspect is use of a chemotherapeutic agent for the manufacture of a medicament for the treatment of glioma in an individual, wherein the treatment comprises administering the chemotherapeutic agent and an immunocytokine to the individual, and wherein the immunocytokine comprises a cytokine conjugated to an antibody molecule that binds the target antigen.

A fifth aspect is an immunocytokine for use in treatment of glioma in an individual, wherein the treatment comprises administering the immunocytokine and a chemotherapeutic agent to the individual, and wherein the immunocytokine comprises a cytokine conjugated to an antibody molecule that binds the target antigen.

A sixth aspect is a chemotherapeutic agent for use in treatment of glioma in an individual, wherein the treatment comprises administering the chemotherapeutic agent and an immunocytokine to the individual, and wherein the immunocytokine comprises a cytokine conjugated to an antibody molecule that binds the target antigen.

A seventh aspect is a medicament comprising an immunocytokine and a chemotherapeutic agent, for use in treatment of glioma in an individual, wherein the treatment comprises administering the medicament to the individual, and wherein the immunocytokine comprises a cytokine conjugated to an antibody molecule that binds the target antigen.

A third development of the invention relates to an improvement to the known anti-tenascin C antibody 4A1-F16 ("F16"). F16 was described in WO2006/050834 and in other publications cited above.

As disclosed herein, an improved F16 antibody has now been produced, which increases expression yield of the antibody and facilitates its production, especially large-scale production on a commercial scale.

The inventors discovered that by making a single amino acid change in VH CDR1 of the F16 VH domain, yield was significantly improved and a high binding affinity was retained.

Accordingly, an aspect of the invention is an antibody molecule comprising a VH CDR1 sequence SEQ ID NO: 18. The antibody molecule may comprise an antibody VH domain having a set of CDRs VH CDR1, VH CDR2 and VH CDR3 wherein VH CDR1 is SEQ ID NO: 18, VH CDR2 is SEQ ID NO: 6 and VH CDR3 is SEQ ID NO: 7. Alternatively the antibody molecule may be a variant comprising up to five (e.g. one or two) amino acid mutations in the VH CDR2 and/or VH CDR3 sequence. The antibody molecule may comprise a VH domain SEQ ID NO: 17 or a variant thereof having up to five amino acid mutations (in the framework and/or CDR 1 or 2), wherein VH CDR1 is SEQ ID NO: 18. The antibody molecule may further comprise the F16 VL domain SEQ ID NO: 4 or a variant thereof as described herein, e.g. an F16 VL domain with up to five amino acid mutations (e.g. one or two). The antibody molecule is preferably an scFv antibody molecule.

These antibody molecules may be employed in other aspects of the invention as a whole, and thus may be provided in immunocytokines for use in aspects of the invention described herein.

Nucleic acids, e.g. vectors, encoding the antibody molecules and immunocytokines described herein are also an aspect of the invention. One aspect is a nucleic acid vector comprising a nucleotide sequence encoding an immunocytokine as described herein.

Nucleic acid and/or antibody molecules of the present invention may be provided in isolated and/or purified form.

Aspects of the first, second and third developments of the invention are described in more detail below.

DETAILED DESCRIPTION

A chemotherapeutic agent is a cytotoxic compound which inhibits the proliferation of tumour or cancer cells. Chemotherapeutic agents may, in some circumstances, have a cytotoxic effect on normal (non-cancerous and non-tumour) cells in a patient.

Alkylating agents are a known category of chemotherapeutic agents, which exert their cytotoxic effect by attaching an alkyl group to DNA. Alkylating agents may attach alkyl groups, e.g. methyl groups, to DNA bases. This may result in DNA fragmentation, cross-linking between DNA strands and/or DNA mutation. Examples of alkylating agents include:
nitrogen mustards (e.g. chlorambucil, chlormethine, cyclophosphamide, ifosfamide, melphalan, bendamustine, trofosfamide, uramustine, mechlorethamine), hydrazines (e.g. procarbazine),
ethyleneimines and methylmelamines (e.g. hexamethylmelamine, thiotepa) alkyl sulphonates (e.g. busulfan, mannosulfan, treosulfan),
triazenes and imidazotetrazines (e.g. dacarbazine, procarbazine, temozolomide, mitozolomide),
aziridines (carboquone, thioTEPA, triaziquone, triethylenemelamine)
nitrosureas (e.g. carmustine, fotemustine, lomustine, nimustine, prednimustine, ranimustine, semustine, streptozocin)
platinum compounds (e.g. carboplatin, cisplatin, nedaplatin, oxaliplatin, triplatin tetranitrate and satraplatin).

Chemotherapeutic agents may be active cytotoxic agents they may be or prodrugs that are hydrolysed or metabolised to active cytotoxic agents.

Preferably the alkylating agent is a triazene or imidazotetrazine. As exemplified in the experimental examples herein, the alkylating agent may be temozolomide, i.e. (8-carbamoyl-3-methylimidazo[5,1-d]-1,2,3,5-tetrazin-4(3H)-one). Temozolomide is a prodrug and is chemically related to dacarbazine but, unlike dacarbazine, it spontaneously hydrolyzes to the intermediate species methyltriazen-1-yl imidazole-4-carboxamide (MTIC) MTIC above pH 7 without requiring metabolism by the liver. MTIC degrades to an active cation, which methylates guanines in DNA at the $O_6$ position. Temozolomide and its use as a chemotherapeutic agent is described in ref. [34].

Tumours that may be treated using the present invention may be cancerous tumours. The tumour or cancer may be in any area of the body, for example the brain. Cancers that may be treated include sarcomas, skin cancer, bladder cancer, breast cancer, uterine cancer, ovarian cancer, prostate cancer, lung cancer, colorectal cancer, cervical cancer, liver cancer, head and neck cancer, oesophageal cancer, pancreatic cancer, renal cancer, stomach cancer and cerebral cancer. Non-cancerous tumours of any of these tissues may also be treated. Cancers may be familial or sporadic.

The tumour may be a tumour of the central nervous system. The tumour may be a brain tumour, such as glioma, e.g. glioblastoma. The term "glioma" refers to tumours of glial cell origin and includes astrocytomas, oligodendrogliomas, ependimomas, and mixed gliomas [35]. They account for more than 70% of all brain tumours and their prognosis is very poor. Glioblastoma is the most frequent (65% of all gliomas) and also the most malignant histological type [36].

The antibody moiety in the immunocytokine of the present invention may bind an antigen of the tumour cells or the tumour neovasculature. The antigen may be an antigen of the extracellular matrix, e.g. the subendothelial extracellular matrix. The antigen may be expressed on cells of the tumour or tumour vasculature. Thus, antigens exposed on the membrane of tumour cells may be targeted using antibody molecules of the invention.

The target antigen may be a tumour associated antigen and/or an antigen of the tumour neovasculature. Preferably, the antigen is an antigen of the tumour neovasculature, e.g. the subendothelial extracellular matrix. The target antigen is preferably differentially expressed in the tumour or tumour neovasculature compared with normal tissue. The antigen may be an isoform of a protein, wherein the isoform is differentially expressed in the tumour or tumour neovasculature compared with normal tissue.

Examples of antigens of the tumour neovasculature such as tenascin-C and fibronectin are described in detail elsewhere herein and any may be a target for the antibody of the present invention.

Preferred antibodies bind preferentially to tumour tissue relative to normal tissue. Antibodies may, for example, bind to stroma and/or neo- and peri-vascular structures of tumour tissue preferentially to normal tissue.

The antibody molecule may bind to fibronectin, e.g. an isoform of fibronectin that is differentially expressed in the tumour neovasculature compared with normal tissue. For example, the antibody molecule may bind a domain of fibronectin that is expressed in isoforms associated with neoplasms, e.g. extra domain B (ED-B).

The antibody may bind tenascin-C, e.g. the large isoform of tenascin-C. The antibody may bind preferentially to tenascin-C large isoform relative to tenascin-C small isoform. Preferably the antibody binds a domain of tenascin-C which are subject to alternative splicing and are expressed only in the large isoform, e.g. any of domains A1 to D (see FIG. 1).

The antibody moiety of the immunocytokine may bind domain A1 of tenascin-C large isoform.

Examples of suitable antibodies for use in immunocytokines of the invention are disclosed in WO2006/050834.

In some embodiments, the antibody moiety of an immunocytokine as described herein competes for binding to tenascin-C with an antibody comprising the 4A1-F16 VH domain SEQ ID NO: 2 and the 4A1-F16 VL domain SEQ ID NO: 4. Competition between antibodies may be assayed easily in vitro, for example using ELISA and/or by tagging a specific reporter molecule to one antibody which can be detected in the presence of other untagged antibody(s), to enable identification of antibodies which bind the same epitope or an overlapping epitope.

The antibody 4A1-F16 has VH and VL domain amino acid sequences and CDRs as shown in the appended sequence listing, as follows:
VH domain SEQ ID NO: 2 or SEQ ID NO: 17
VL domain SEQ ID NO: 4

VH CDR1 SEQ ID NO: 5 or SEQ ID NO: 18
VH CDR2 SEQ ID NO: 6
VH CDR3 SEQ ID NO: 7
VL CDR1 SEQ ID NO: 8
VL CDR2 SEQ ID NO: 9
VL CDR3 SEQ ID NO: 10

The alternative VH domain sequences of F16, SEQ ID NO: 2 and SEQ ID NO: 17, differ by one amino acid in VH CDR1. Thus, alternative VH CDR1 sequences of F16 are SEQ ID NO: 5 and SEQ ID NO: 18.

SEQ ID NO: 5, RYGAS, was the original VH CDR1 sequence of the clone 4A1-F16. However, the inventors discovered that by mutating the Ala to Met in position 4 of the VH CDR1, the expression yield of the antibody could be significantly increased while still retaining high affinity binding to tenascin-C. Accordingly, 4A1-F16 having the Ala to Met mutation in SEQ ID NO: 5, to provide the VH CDR1 sequence SEQ ID NO: 18, represents an improved variant of F16. In the present application, either of these variants of F16 may be used.

A suitable antibody for use in an immunocytokine as described herein comprises an antibody antigen binding site comprising a VH domain and a VL domain,
  the VH domain comprising a VH CDR1 SEQ ID NO: 5 or SEQ ID NO: 18, a VH CDR2 SEQ ID NO: 6 and a VH CDR3 SEQ ID NO: 7; and
  the VL domain comprising a VL CDR1 SEQ ID NO: 8, a VL CDR2 SEQ ID NO: 9 and a VL CDR3 SEQ ID NO: 10.

The antibody may comprise an antibody antigen binding site comprising the 4A1-F16 VH domain of SEQ ID NO: 2 or SEQ ID NO: 17 and the 4A1-F16 VL domain of SEQ ID NO: 4.

In a preferred embodiment, the antibody molecule comprises a VH domain comprising a VH CDR1, VH CDR2 and VH CDR3 wherein:
  VH CDR1 is SEQ ID NO: 18,
  VH CDR2 is SEQ ID NO: 6, and
  VH CDR 3 is SEQ ID NO: 7.

Preferably, an antibody molecule in the present invention comprises a VL domain comprising a VL CDR1, VL CDR2 and a VL CDR3 wherein
  VL CDR1 is SEQ ID NO: 8,
  VL CDR2 is SEQ ID NO: 9, and
  VL CDR3 is SEQ ID NO: 10.

Variants of these VH and VL domains and CDRs may also be employed in antibodies for use in immunocytokines as described herein as described herein. Suitable variants can be obtained by means of methods of sequence alteration or mutation and screening.

Particular variants for use as described herein may include one or more amino acid sequence alterations (addition, deletion, substitution and/or insertion of an amino acid residue), maybe less than about 20 alterations, less than about 15 alterations, less than about 10 alterations or less than about 5 alterations, 4, 3, 2 or 1. Alterations may be made in one or more framework regions and/or one or more CDRs. In particular, alterations may be made in VH CDR1, VH CDR2 and/or VH CDR3, especially VH CDR3.

A number of antibody molecule formats are known and any suitable format may be used for the antibody moiety of the immunocytokine. Preferably, the immunocytokine comprises the cytokine conjugated to an scFv antibody molecule.

The antibody molecule may consist of scFv, or it may be a small immunoprotein (SIP) comprising a homodimer of two polypeptides, each polypeptide comprising an scFv fused to an antibody heavy chain constant domain e.g. CH3 or CH4. The scFv may be connected to the constant domain via a linker peptide. Dimerisation of the constant domains forms the homodimer.

The antibody molecule may be a SIP comprising a homodimer of scFv fused to a human CH4 domain of the secretory isoform S2 of human IgE. CH4 is the domain that allows dimerisation in the IgE molecule and the εS2 isoform contains a cysteine at the carboxyterminal end, which stabilises the IgE dimer through an interchain disulphide bond. Thus, a covalent homodimer may be produced.

Preferably, the antibody molecule is an scFv antibody molecule, consisting of a VH domain fused to a VL domain by a peptide linker. The VH domain is normally the N terminal domain, with the VL domain being the C terminal domain. The VH and VL domains are preferably connected by a peptide linker. The linker may be a sequence of about 5 to 10 amino acids. An example peptide linker sequence is SEQ ID NO: 22.

Preferably, the immunocytokine for use as described herein comprises IL2 conjugated to the antibody molecule.

IL2 is a secreted cytokine which is involved in immunoregulation and the proliferation of T and B lymphocytes. IL2 has been shown to have a cytotoxic effect on tumour cells and recombinant human IL2 (aldesleukin: Proleukin®) has FDA approval for treatment of metastatic renal carcinoma and metastatic melanoma. Tumour-targeting immunocytokines based on IL2 have been shown to mediate a massive infiltration of leukocytes into the tumour mass, with NK cells as the main mediator of therapeutic activity [14, 22, 37]. The inventors have recognised that the properties of IL2 may be particularly beneficial for treatment of glioma e.g. for treating glioblastoma [38, 39]. The experiments described herein demonstrate that infiltration of cytotoxic effector cells including NK cells, macrophages and leukocytes into the tumour was markedly increased in glioblastoma treated with a combination of IL2-antibody conjugate and chemotherapy.

The sequence of human IL2 is set out in SEQ ID NO: 11 and publicly available under the Swiss Prot database as P60568. SEQ ID NO: 11 is the precursor sequence including an N-terminal signal peptide of 20 amino acids. Mature human IL2, lacking the signal peptide is residues 21 to 153 of SEQ ID NO: 11, and this mature sequence is set out in SEQ ID NO: 19. The IL2 moiety of the immunocytokine may comprise a sequence of all or part of the IL2 amino acid sequence shown in SEQ ID NO: 11, e.g. all or part of the IL2 amino acid sequence shown in SEQ ID NO: 19. A preferred IL2 sequence comprises SEQ ID NO: 19.

Variants of the SEQ ID NO: 19 amino acid sequence may be used, e.g. natural variants encoded by human alleles and/or variants with one or two amino acid mutations. A mutation may be deletion, substitution, addition or insertion of an amino acid residue.

An IL2 amino acid sequence used in the present invention may have at least 90% sequence identity, at least 95% sequence identity or at least 98% sequence identity to the mature human IL2 sequence set out in SEQ ID NO: 19. Sequence identity is commonly defined with reference to the algorithm GAP (Wisconsin GCG package, Accelerys Inc, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4. Use of GAP may be preferred but other algorithms may be used, e.g. BLAST (which uses the method of Altschul et al. [40]), FASTA (which uses the method of Pearson and Lipman [41]), or the Smith-Waterman algorithm [42], or the TBLASTN program, of Altschul et al. [40], generally employing default parameters. In particular, the psi-Blast algorithm [43] may be used. Sequence identity may be determined with reference to the full length of a sequence set out herein.

Preferably the IL2 moiety of the immunocytokine comprises or consists of the sequence of mature human IL2 set out in SEQ ID NO: 19.

The IL2 moiety may be fused upstream (N-terminal) or downstream (C-terminal) of the antibody molecule or polypeptide component thereof.

The cytokine moiety may be connected or attached to the antibody molecule by any suitable covalent or non-covalent means. In preferred embodiments, the immunocytokine may be a fusion protein comprising the cytokine, e.g. IL2, and the antibody molecule or a polypeptide component thereof (e.g. a heavy chain or a light chain of an antibody or multi-chain antibody fragment, such as a Fab). Thus, for example, the cytokine moiety may be fused to a VH domain or VL domain of the antibody. Typically the antibody molecule, or component thereof, and cytokine moiety are joined via a peptide linker, e.g. a peptide of about 5-25 residues, e.g. 10-20 residues, preferably about 15 residues. Suitable examples of peptide linkers are well known in the art. In some embodiments, a linker may have an amino acid sequence as set out in SEQ ID NO: 12. Normally, the linker has an amino acid sequence comprising one or more tandem repeats of a motif. Typically the motif is a five residue sequence, and preferably at least 4 of the residues are Gly or Ser. Where four of the five residues is Gly or Ser, the other residue may be Ala. More preferably each of the five residues is Gly or Ser. Preferred motifs are GGGGS, SSSSG, GSGSA and GGSGG. Preferably, the motifs are adjacent in the sequence, with no intervening nucleotides between the repeats. The linker sequence may comprise or consist of between one and five, preferably three or four, repeats of the motif. For example, a linker with three tandem repeats may have one of the following amino acid sequences:

| | |
|---|---|
| GGGGSGGGGSGGGGS | SEQ ID NO: 13 |
| SSSSGSSSSGSSSSG | SEQ ID NO: 14 |
| GSGSAGSGSAGSGSA | SEQ ID NO: 15 |
| GGSGGGGSGGGGSGG. | SEQ ID NO: 16 |

The linker may comprise additional residues at the N and/or C terminal end.

A preferred linker sequence is SEQ ID NO: 20—EF-SSSSGSSSSGSSSSG.

Preferably, the IL2 moiety is fused to the C-terminal end of the VL domain of an scFv antibody molecule, preferably by means of a linker peptide.

In a preferred embodiment, the amino acid sequence of the immunocytokine is at least 80%, 90%, 95% or 98% identical to the amino acid sequence SEQ ID NO: 21. This is the sequence of the F16(scFv)-IL2 sequence shown in FIG. 6.

Administration of the chemotherapeutic agent, immunocytokine and compositions comprising one or both of these molecules is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage etc, is within the responsibility of general practitioners and other medical doctors.

The individual to be treated using the present invention may be a mammal, preferably a human.

Treatment of the tumour or cancer in the individual may comprise eradication of the tumour. However, for many forms of tumours, especially malignant cancers and aggressive forms such as glioblastoma, complete cure may not be possible. Treatment may comprise retarding tumour growth and/or reducing tumour volume. Treatment may comprise lengthening the overall survival or progression free survival of the individual. Treatment may comprise improving quality of life of the individual, e.g. by reducing one or more symptoms caused by the tumour. Treatment may comprise inhibiting regrowth of the tumour following tumour regression. As demonstrated in the examples herein, the combination of immunocytokine treatment with the chemotherapeutic agent increased overall survival time, increased progression-free survival time, retarded tumour growth, eradicated tumours and inhibited regrowth of tumours following regression. Treatment according to the present invention may be used to achieve any or all of these therapeutic effects.

The dose of chemotherapeutic agent and immunocytokine administered to the individual will depend upon a number of factors, the size and location of the area to be treated, the nature of the immunocytokine (e.g. whole antibody, fragment or diabody). A typical immunocytokine dose will be in the range 0.5 mg to 100 g for systemic applications, and 10 µg to 1 mg for local applications. This is a dose for a single treatment of an adult patient, which may be proportionally adjusted for children and infants, and also adjusted for other antibody formats in proportion to molecular weight.

Appropriate doses and regimens for chemotherapeutic agents are well known in the art. For temozolomide, the daily dose may be about 75 mg per square meter of body surface area, followed by a maintenance regimen of 150-200 $mg/m^2$ daily for 5 days of every 28 day cycle, repeated for 6 cycles [44]. Treatments may be repeated at daily, twice-weekly, weekly or monthly intervals, at the discretion of the physician.

The immunocytokine and the chemotherapeutic agent may be administered separately, and administration may be sequential or simultaneous, in accordance with any suitable regimen. The immunocytokine and the chemotherapeutic agent will usually be administered to an individual in the form of pharmaceutical compositions, which may comprise at least one component in addition to the active compound.

Suitable components include a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous. The immunocytokine and the chemotherapeutic agent may be formulated in separate pharmaceutical compositions or, where appropriate, in the same pharmaceutical composition.

Medicaments or pharmaceutical compositions comprising an immunocytokine and a chemotherapeutic agent according to the present invention can be produced for use in treatment of a tumour in an individual. A methods of making a medicament or pharmaceutical composition for use in the treatment of a tumour is an aspect of the invention. The method may comprise formulating the chemotherapeutic agent and the immunocytokine into a composition comprising one or more pharmaceutically acceptable excipients. The composition may comprise separate formulations of the chemotherapeutic agent and immunocytokine, or a combined formulation.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

A kit may be provided for use in the treatment of a tumour in an individual, the kit comprising a chemotherapeutic agent according to the invention and an immunocytokine according to the invention. The components of the kit (i.e. the chemotherapeutic agent and immunocytokine) are preferably sterile and in sealed phials or other containers. A kit may further comprise instructions for use of the components in a method described herein. The components of the kit may be separately packaged. The components may be comprised or packaged in a container, for example a bag, box, jar, tin or blister pack.

TERMINOLOGY

Antibody Molecule

This describes an immunoglobulin whether natural or partly or wholly synthetically produced. The term also covers any polypeptide or protein comprising an antibody antigen-binding site.

Antibody fragments that comprise an antibody antigen-binding site include, but are not limited to, molecules such as Fab, Fab', Fab'-SH, scFv, Fv, dAb and Fd. Various other antibody molecules including one or more antibody antigen-binding sites have been engineered, including for example Fab$_2$, Fab$_3$, diabodies, triabodies, tetrabodies and minibodies. Antibody molecules and methods for their construction and use are described in ref. [45].

It is possible to take monoclonal and other antibodies and use techniques of recombinant DNA technology to produce other antibodies or chimeric molecules that bind the target antigen. Such techniques may involve introducing DNA encoding the immunoglobulin variable region, or the CDRs, of an antibody to the constant regions, or constant regions plus framework regions, of a different immunoglobulin. See, for instance, EP-A-184187, GB 2188638A or EP-A-239400, and a large body of subsequent literature. A hybridoma or other cell producing an antibody may be subject to genetic mutation or other changes, which may or may not alter the binding specificity of antibodies produced.

As antibodies can be modified in a number of ways, the term "antibody molecule" should be construed as covering any binding member or substance having an antibody antigen-binding site with the required specificity and/or binding to antigen. Thus, this term covers antibody fragments and derivatives, including any polypeptide comprising an antibody antigen-binding site, whether natural or wholly or partially synthetic. Chimeric molecules comprising an antibody antigen-binding site, or equivalent, fused to another polypeptide (e.g. derived from another species or belonging to another antibody class or subclass) are therefore included. Cloning and expression of chimeric antibodies are described in EP-A-0120694 and EP-A-0125023, and a large body of subsequent literature.

Preferably, the antibody molecules used in the invention are human or humanised antibody molecules.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment [46, 47, 48], which consists of a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site [49, 50]; (viii) bispecific single chain Fv dimers (PCT/US92/09965) and (ix) "diabodies", multivalent or multispecific fragments constructed by gene fusion (WO94/13804; [51]). Fv, scFv or diabody molecules may be stabilized by the incorporation of disulphide bridges linking the VH and VL domains [52]. Minibodies comprising a scFv joined to a CH3 domain may also be made [53]. Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

Qui et al. [54] described antibody molecules containing just two CDRs linked by a framework region. CDR3 from the VH or VL domain was linked to the CDR1 or CDR2 loop of the other domain. Linkage was through the C terminus of the selected CDR1 or CDR2 to the N terminus of the CDR3, via a FR region. Qui et al. selected the FR region having the fewest hydrophobic patches. The best combination for the antibody tested was found to be VL CDR1 linked by VH FR2 to VH CDR3 (VHCDR1-VHFR2-VLCDR3). At a molecular weight of around 3 kDa, these antibody molecules offer advantages in terms of improved tissue penetration as compared with full immunoglobulins (approx. 150 kDa) or scFv (approx. 28 kDa).

Antibody fragments of the invention can be obtained starting from a parent antibody molecule by methods such as digestion by enzymes e.g. pepsin or papain and/or by cleavage of the disulfide bridges by chemical reduction. In another manner, the antibody fragments comprised in the present invention can be obtained by techniques of genetic recombination likewise well known to the person skilled in the art or else by peptide synthesis by means of, for example, automatic peptide synthesizers, such as those supplied by the company Applied Biosystems, etc., or by nucleic acid synthesis and expression.

Functional antibody fragments according to the present invention include any functional fragment whose half-life is increased by a chemical modification, especially by PEGylation, or by incorporation in a liposome.

A dAb (domain antibody) is a small monomeric antigen-binding fragment of an antibody, namely the variable region of an antibody heavy or light chain [48]. VH dAbs occur naturally in camelids (e.g. camel, llama) and may be produced by immunizing a camelid with a target antigen, isolating antigen-specific B cells and directly cloning dAb genes from individual B cells. dAbs are also producible in cell culture. Their small size, good solubility and temperature stability makes them particularly physiologically useful and suitable for selection and affinity maturation. Camelid VH dAbs are being developed for therapeutic use under the name "Nanobodies™". An antibody molecule of the present invention may be a dAb. The antibody molecule comprise a VH or VL domain substantially as set out herein, or a VH or VL domain comprising a set of CDRs substantially as set out herein.

As used herein, the phrase "substantially as set out" refers to the characteristic(s) of the relevant CDRs of the VH or VL domain of antibody molecules described herein will be either identical or highly similar to the specified regions of which the sequence is set out herein. As described herein, the phrase "highly similar" with respect to specified region(s) of one or more variable domains, it is contemplated that from 1 to about 5, e.g. from 1 to 4, including 1 to 3, or 1 or 2, or 3 or 4, amino acid substitutions may be made in the CDR and/or VH or VL domain.

Bispecific or bifunctional antibodies form a second generation of monoclonal antibodies in which two different variable regions are combined in the same molecule [55]. Their use has been demonstrated both in the diagnostic field and in the therapy field from their capacity to recruit new effector functions or to target several molecules on the surface of tumour cells. Where bispecific antibodies are to be used, these may be conventional bispecific antibodies, which can be manufactured in a variety of ways [56], e.g. prepared chemically or from hybrid hybridomas, or may be any of the bispecific antibody fragments mentioned above. These antibodies can be obtained by chemical methods [57, 58] or somatic methods [59, 60] but likewise and preferentially by genetic engineering techniques which allow the heterodimerization to be forced and thus facilitate the process of purification of the antibody sought [61]. Examples of bispecific antibodies include those of the BiTE™ technology in which the binding domains of two antibodies with different specificity can be used and directly linked via short flexible peptides. This combines two antibodies on a short single polypeptide chain. Diabodies and scFv can be constructed without an Fc region, using only variable domains, potentially reducing the effects of anti-idiotypic reaction.

Bispecific antibodies can be constructed as entire IgG, as bispecific Fab'2, as Fab'PEG, as diabodies or else as bispecific scFv. Further, two bispecific antibodies can be linked using routine methods known in the art to form tetravalent antibodies.

Bispecific diabodies, as opposed to bispecific whole antibodies, may also be particularly useful because they can be readily constructed and expressed in E. coli. Diabodies (and many other polypeptides, such as antibody fragments) of appropriate binding specificities can be readily selected using phage display (WO94/13804) from libraries. If one arm of the diabody is to be kept constant, for instance, with a specificity directed against the antigen of the tumour neovasculature, then a library can be made where the other arm is varied and an antibody of appropriate specificity selected. Bispecific whole antibodies may be made by alternative engineering methods as described in Ridgeway et al., 1996 [62].

Various methods are available in the art for obtaining antibodies against a target antigen. The antibodies may be monoclonal antibodies, especially of human, murine, chimeric or humanized origin, which can be obtained according to the standard methods well known to the person skilled in the art.

In general, for the preparation of monoclonal antibodies or their functional fragments, especially of murine origin, it is possible to refer to techniques which are described in particular in the manual "Antibodies" [63] or to the technique of preparation from hybridomas described by Köhler and Milstein [64].

Monoclonal antibodies can be obtained, for example, from an animal cell immunised against the target antigen or one of its fragments containing the epitope recognised by the monoclonal antibodies. Suitable fragments and peptides or polypeptides comprising them are described herein, and may be used to immunise animals to generate antibodies against a target antigen. Said antigen, or one of its fragments, can especially be produced according to the usual working methods, by genetic recombination starting with a nucleic acid sequence contained in the cDNA sequence coding for the antigen or fragment thereof, by peptide synthesis starting from a sequence of amino acids comprised in the peptide sequence of the antigen and/or fragment thereof.

The monoclonal antibodies can, for example, be purified on an affinity column on which the antigen or one of its fragments containing the epitope recognised by said monoclonal antibodies, has previously been immobilised. More particularly, the monoclonal antibodies can be purified by chromatography on protein A and/or G, followed or not followed by ion-exchange chromatography aimed at eliminating the residual protein contaminants as well as the DNA and the LPS, in itself, followed or not followed by exclusion chromatography on Sepharose gel in order to eliminate the potential aggregates due to the presence of dimers or of other multimers. In one embodiment, the whole of these techniques can be used simultaneously or successively.

Antigen-Binding Site

This describes the part of a molecule that binds to and is complementary to all or part of the target antigen. In an antibody molecule it is referred to as the antibody antigen-binding site, and comprises the part of the antibody that binds to and is complementary to all or part of the target antigen. Where an antigen is large, an antibody may only bind to a particular part of the antigen, which part is termed an epitope. An antibody antigen-binding site may be provided by one or more antibody variable domains. An antibody antigen-binding site may comprise an antibody light chain variable region (VL) and an antibody heavy chain variable region (VH).

WO2006/072620 describes engineering of antigen binding sites in structural (non-CDR) loops extending between beta strands of immunoglobulin domains. An antigen binding site may be engineered in a region of an antibody molecule separate from the natural location of the CDRs, e.g. in a framework region of a VH or VL domain, or in an antibody constant domain e.g. CH1 and/or CH3. An antigen binding site engineered in a structural region may be additional to, or instead of, an antigen binding site formed by sets of CDRs of a VH and VL domain. Where multiple antigen binding sites are present in an antibody molecule, they may bind the same antigen (target antigen), thereby increasing valency of the antibody molecule. Alternatively, multiple antigen binding sites may bind different antigens (the target antigen and one or more another antigen), and this may be used to add effector functions, prolong half-life or improve in vivo delivery of the antibody molecule.

It is convenient to point out here that "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Certain aspects and embodiments of the invention will now be illustrated by way of example. All documents and database entries mentioned in this specification are incorporated herein by reference in their entirety.

EXPERIMENTS

Summary

Figure 1:
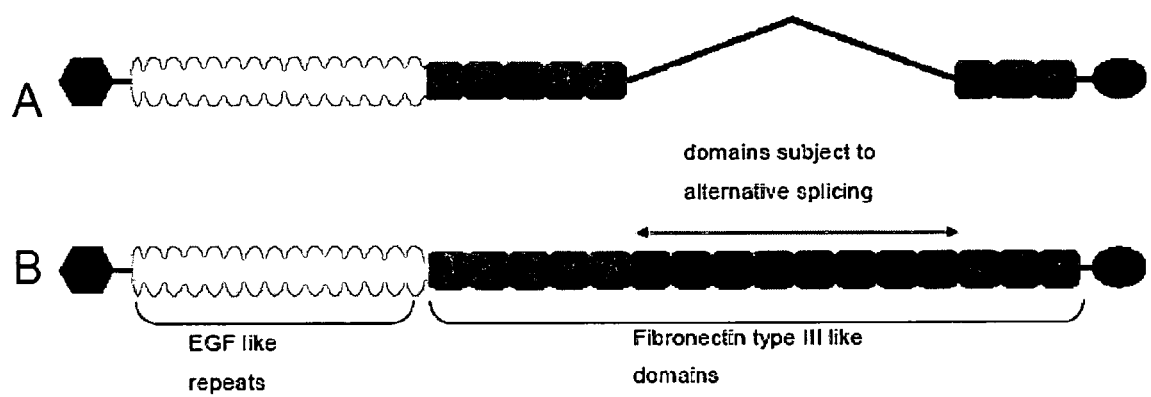
FIG. 1 shows a schematic representation of the small (A) and large (B) tenascin-C isoform. Several fibronectin type III like domains are subject to alternative splicing, either being included (B) or omitted (A) in the molecule. The amino acid sequence and encoding nucleotide sequence of tenascin C are publically available under sequence database references NP_002151.1 GI:4504549 and NM_002160.1 GI:4504548, respectively.

The experiments below describe therapeutic properties of temozolomide in combination with F16-IL2 for the therapy of experimental murine models of human glioblastoma. The F16-IL2 used in this study is a clinical-stage immunocytokine consisting of human IL-2 fused to the human antibody F16, specific to the A1 domain of tenascin-C.

A radiolabelled preparation of the fusion protein F16-IL2 was shown to preferentially accumulate in subcutaneously grafted human U87 gliomas in nude mice, using quantitative biodistribution analysis. When co-administered with temozolomide, F16-IL2 induced a complete remission of established subcutaneous human U87 gliomas in nude mice, which remained tumour-free for over 200 days.

Materials and Methods

Immunohistochemistry on Human Glioblastoma Samples and on Glioblastoma Xenografts Freshly frozen human glioblastoma tissues were received from the Neurosurgery department of Basel University Hospital, Basel, Switzerland, and were stored at −80° C.

For immunohistochemical procedures, the F16 antibody was used in biotinylated small immunoprotein (SIP) format. F16 is a human monoclonal antibody specific to the extra-domain A1 of tenascin C [25]. It was obtained from the ETH2 phage display libraries, underwent affinity maturation, had a dissociation constant in the low nanomolar range, and exhibited a kinetic dissociation constant koff towards the respective cognate antigens <10-2 s-1 in real-time interaction analysis experiments performed on a BIAcore 3000 instrument (GE Healthcare, Otelfingen). The SIP antibody format consists of a covalent homodimer in which each monomeric unit comprises a scFv fused to a human CH4 domain of the secretory isoform S2 of human IgE (as exemplified for antibody L19 in ref. [65]). This domain promotes the formation of homodimers that are further stabilized by disulfide bonds between the C-terminal cysteine residues, resulting in a 75 kDa homobivalent miniantibody. This SIP antibody was further biotinylated in order to avoid background staining given by the human endogenous IgE.

Sections of 10 μm thickness were treated with ice-cold acetone, rehydrated in TBS (50 mM Tris, 100 mM NaCl, 0.001% Aprotinin, pH 7.4) and blocked with TBS 20% fetal calf serum. Biot-(SIP) F16 antibody was added onto the sections in a final concentration of 2 μg/ml. Bound antibody was detected with streptavidin-alkaline phosphatase complex (Biospa). Fast Red (Tablets Set, Sigma) was used as phosphatase substrate and sections were counterstained with Gill's hematoxylin no. 2 (Sigma). For every immunohistochemical experiment, in addition to staining with the F16 antibody, a negative control was performed by omitting the primary antibody. Finally, L19, a proven glioma-targeting antibody against the extra-domain B of fibronectin [30], was used as positive control on the same tissue sections and at identical final concentration (2 μg/ml).

An optic microscope (Zeiss) was used to evaluate the expression of the A1 domain of tenascin C and of the EDB domain of fibronectin, as revealed by the staining given by the F16 and L19 antibodies respectively.

Cell Lines and Animals

Human subcutaneous glioblastoma xenografts were created with the U87 cell line (already present in the lab). Cells were cultured in MEM (Invitrogen, Basel, Switzerland), supplemented with 10% FCS (Invitrogen), 2 mM L-glutamine, 1 mM sodium pyruvate, 100 U/mL ampicillin and incubated at 37° C. in 5% $CO_2$. For the subcutaneous study, eight-week-old female Balb/c nude mice were purchased from Charles River Laboratories (Sulzfeld, Germany).

Antibodies and Therapeutic Agents

The F16 antibody, specific to the extra-domain A1 of tenascin-C, has been described before [25]. The expression, purification and characterization of the F16-IL2 fusion protein has also been described [22]. F16-IL2 was purchased from Philogen (Siena, Italy) and temozolomide from ABCR GmbH & Co. KG (Karlsruhe, Germany). Temozolomide was dissolved in saline 10% DMSO solution in a concentration of 3.5 mg/ml.

Biodistribution Experiments

The in vivo targeting performance of F16-IL2 was evaluated by quantitative biodistribution analysis [14]. Briefly, female BALB/c nude mice bearing subcutaneous U87 tumours (obtained by a s.c. flank injection of 5×106 U87 cells) were grouped (n=5) when tumours were clearly palpable (volume of ca. 200 mm3) and injected i.v. into the lateral tail vein with radioiodinated F16-IL2. Antibody immunoreactivity after labelling was evaluated by loading a sample of radiolabelled F16-IL2 onto TNC-A1-Sepharose resin, followed by radioactive counting of the flow-through and of the eluate fractions. Immunoreactivity, defined as the ratio between the counts of the eluted protein and the sum of the counts of the eluted and flow-through fractions, was 84%. Mice were sacrificed 24 hours after injection of F16-IL2 (10 μg, 3.6 μCi per mouse). Organs were weighed and radioactivity was counted with a Packard Cobra gamma counter. Radioactivity content of representative organs was expressed as the percentage of the injected dose per gram of tissue (% ID/g).

Subcutaneous Glioma Mouse Models

Subcutaneous glioblastoma bearing mice were obtained by a s.c. flank injection of 5×106 U87 cells in 8-week old female BALB/c nude mice [66]. Twelve days after tumour cell implantation, when tumours had reached a size of 250-300 mm$^3$, mice were staged to maximize uniformity among the groups (n=5).

One group was injected i.v. (lateral tail vein) with 20 μg of F16-IL2 (corresponding to 6.6 μg of IL2) in a total volume of 100 μl PBS solution (Phosphate Buffer Saline), one was injected i.p. with 0.525 mg of temozolomide (corresponding to 75 mg/m$^2$) in a total volume of 150 μl saline 10% DMSO solution, a third group received both the i.v. injection of 20 μg F16-IL2 and the i.p. of 0.525 mg temozolomide, finally, the control group was injected i.p. with 150 μl of saline 10% DMSO.

A schedule of five total administrations was established: on days 12, 15, 18, 21, 24 from the tumour cell injection into mice (day 0).

Dosage of F16-IL2 was in line with the recommended human dose of 18 million I.U. of recombinant IL2 (Proleukin, Novartis) and of 22.5 million I.U. of IL2 equivalents, used in clinical trials with the immunocytokine L19-IL2.

A 75 mg/m$^2$ dose of temozolomide was chosen in order to mimic the standard of care for newly diagnosed glioblastoma patients [44] with immunotherapy instead of the radiation treatment.

Radiotherapy was avoided in order to evaluate the efficacy of F16-IL2 and temozolomide combined together. The five-administration schedule reflected the intent to mimic the daily temozolomide treatment in patients (75 mg/m$^2$ daily for 6 weeks) [44]. The five-administration 75 mg/m$^2$ temozolomide schedule was far below the $LD_{10}$ for the subcutaneous glioma mouse models [67].

Mice were monitored daily and tumours were measured with a digital caliper three times per week. Tumour volume was estimated using the formula: volume=length×width$^2$/2. Animals were sacrificed when tumours approached a volume of 3,000 mm$^3$ or when tumours turned necrotic and bleeding, according to the Swiss regulations and under a project license granted by the Veterinäramt des Kantons Zürich (198/2005). No animals had to be sacrificed because of suffering from side-effects of the malignancy or from therapy-derived toxicities.

Immunofluorescence Assessment of Tumour-Infiltrating Cells and of Microvascular Density in Subcutaneous Glioma Xenografts To evaluate the role of inflammatory cell responses in vivo, female Balb/c nude mice bearing s.c. U87 tumours (3 mice per group) were treated on days 12, 15 and 18 after tumour cell implantation with either saline 10% DMSO (i.p.), F16-IL2 (i.v.), temozolomide (i.p.), and F16-IL2 (i.v.) plus temozolomide (i.p.). Mice were sacrificed 24 hours after the third injection, and tumours were excised and snap-frozen in OCT. The immunofluorescent staining of tumour sections was performed using antibodies against the following antigens: F4/80 (rat anti-mouse F4/80, clone A3-1, AbCam, Cambridge, UK) for the detection of tumour-infiltrating macrophages, asialo GM1 (rabbit anti-asialo GM1, Wako Pure Chemical Industries Ltd, Osaka, Japan) for NK cells, CD45 (rat anti-mouse CD45, BD Biosciences Pharmingen, Allschwil, Switzerland) for leukocytes, CD31 (rabbit or rat anti-mouse CD31, BD Pharmingen, Allschwil, Switzerland) for the localization of endothelial cells, and IL2 (rat anti-human IL2, eBioscience Inc, San Diego, USA) for the detection of the F16-IL2 immunocytokine in the F16-IL2 and in the F16-IL2+temozolomide therapeutic groups.

Sections of 10 μm thickness were treated with ice-cold acetone, rehydrated in PBS and blocked with PBS 10% donkey serum+10% goat serum. Sections were then incubated with the primary antibodies (in a PBS 12% BSA solution) rat anti-mouse F4/80+rabbit anti-mouse CD31, rabbit anti-asialo GM1+rat anti-mouse CD31, rat anti-mouse CD45+rabbit anti-mouse CD31, and rat anti-human IL2+rabbit anti-mouse CD31, in order to evaluate the distribution of macrophages, NK cells, and leukocytes in relation with the tumour vasculature in every therapeutic group (placebo, F16-IL2, temozolomide, F16-Il2+temozolomide). The location of the F16-IL2 fusion protein within the tumour was examined in the F16-IL2 and in the F16-Il2+temozolomide therapeutic groups. Bound antibody was detected with fluorescent Alexa488- or Alexa594-coupled secondary antibodies (donkey anti-rat or goat anti-rabbit, BD Biosciences Pharmingen) and DAPI in a PBS 12% BSA solution.

In each tumour section, the staining given by the primary antibodies was quantified in three representative 10× microscopic images using the ImageJ software (http://rsb.info.nih.gov/ij/).

Statistical Analysis

Biodistribution data are expressed as the median ±SD. Tumour volumes are shown as average ±SD or SE. Kaplan-Meier survival curves were performed to display therapeutic efficacy in the subcutaneous glioma model.

Results

Immunohistochemistry on Human Glioblastoma Specimens and on Mouse Xenografts

Expression of A1 domain of tenascin-C and of the EDB domain of fibronectin was assessed in sections of glioblastoma surgical specimens and of U87 gliomablastomas grafted subcutaneously in nude mice. Identical concentrations of the F16 and L19 antibodies were used, in full analogy to the recently published comparative analysis of antigen expression in thoracic neoplasias. The F16 antibody was found to strongly stain both experimental U87 tumours and glioblastomas from patients, with patterns and intensities comparable to the ones of the L19 antibody, which had previously been shown to stain blood vessels in virtually all types of high-grade astrocytomas [30].

Biodistribution Studies with Radiolabelled F16-IL2

Figure 2:
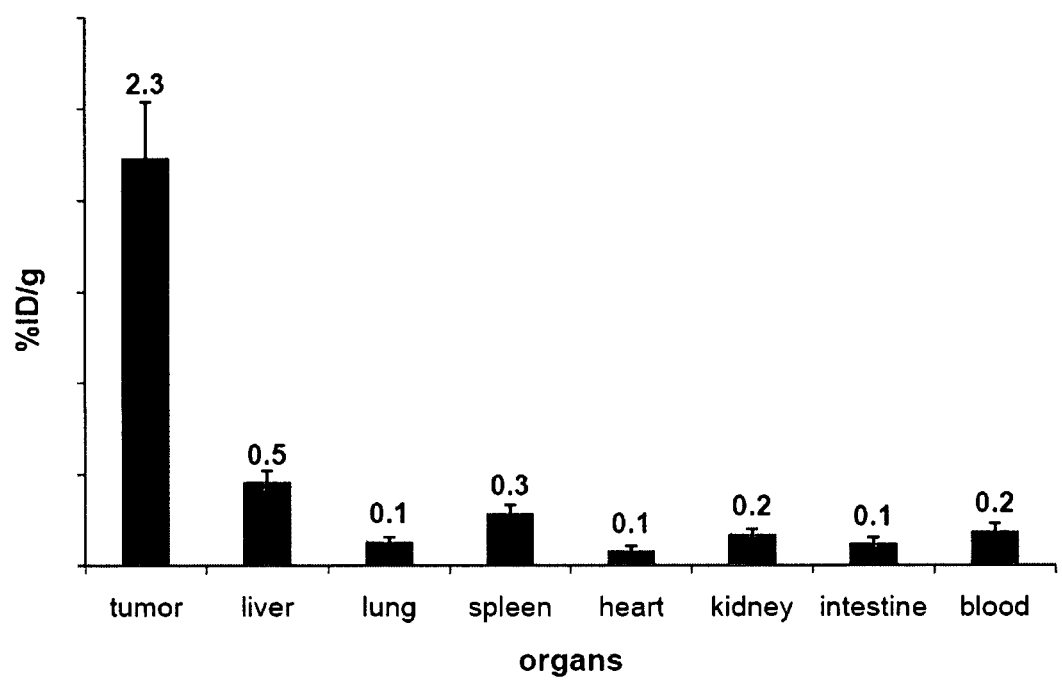
FIG. 2 shows radioactivity content of representative organs was expressed as the percentage of the injected dose per gram of tissue (% ID/g), following intravenous injection of mice with a radioiodinated preparation of F16-IL2.

Mice bearing subcutaneous U87 glioblastomas were injected i.v. with radioiodinated preparations of F16-IL2, in order to study in vivo targeting performance by quantitative biodistribution analysis. The immunocytokine displayed a preferential accumulation in the tumour 24 h after injection (2.3% ID/g), with a tumour-to-blood ratio of 11.5 and with excellent tumour:organ ratios (FIG. 2).

Therapeutic Activity of F16-IL2 Combined with Temozolomide in Subcutaneous Glioblastoma Models Therapeutic activity of temozolomide and of F16-IL2 (alone and in combination) was compared in nude mice bearing subcutaneous U87 tumours. Therapy was started 12 days after subcutaneous injection of U87 cells, when tumours had reached an average size of 300 mg. Temozolomide was administered five times with i.p. injections of 0.525 mg in 10% DMSO solution every three days. F16-IL2 was administered i.v. at 20 μg doses.

Figure 3:
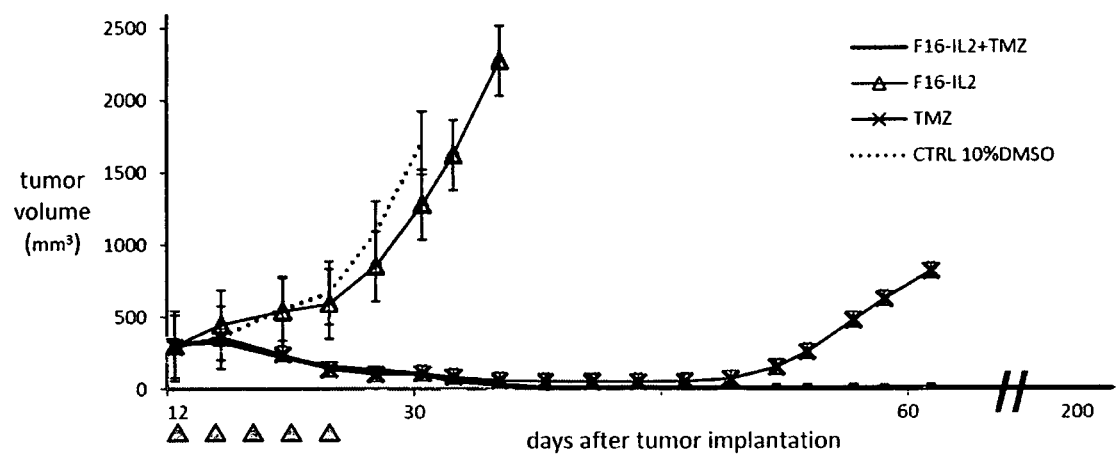
FIG. 3 shows volume of tumours over time in the mouse subcutaneous model of human glioblastoma.

Monotherapy treatment with F16-IL2 led only to a minor tumour growth retardation, compared to the control group of mice treated with 10% DMSO, while all mice in the temozolomide group exhibited a virtually complete tumour regression by day 30. However, by day 45, tumours started growing again in 3/5 mice of this treatment group. By contrast, mice treated with a combination of temozolomide and F16-IL2 exhibited a complete tumour eradication and remained tumour-free for over 200 days. See FIG. 3.

Figure 5:
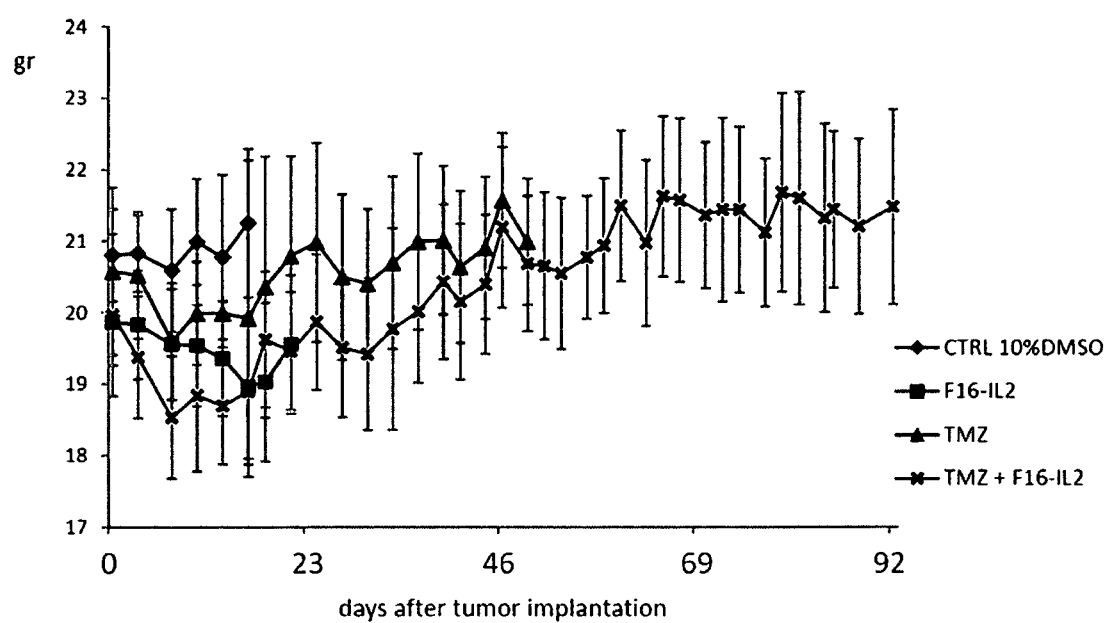
FIG. 5 shows body weight of mice in the four treatment groups in the subcutaneous model of human glioblastoma.
Figure 6:
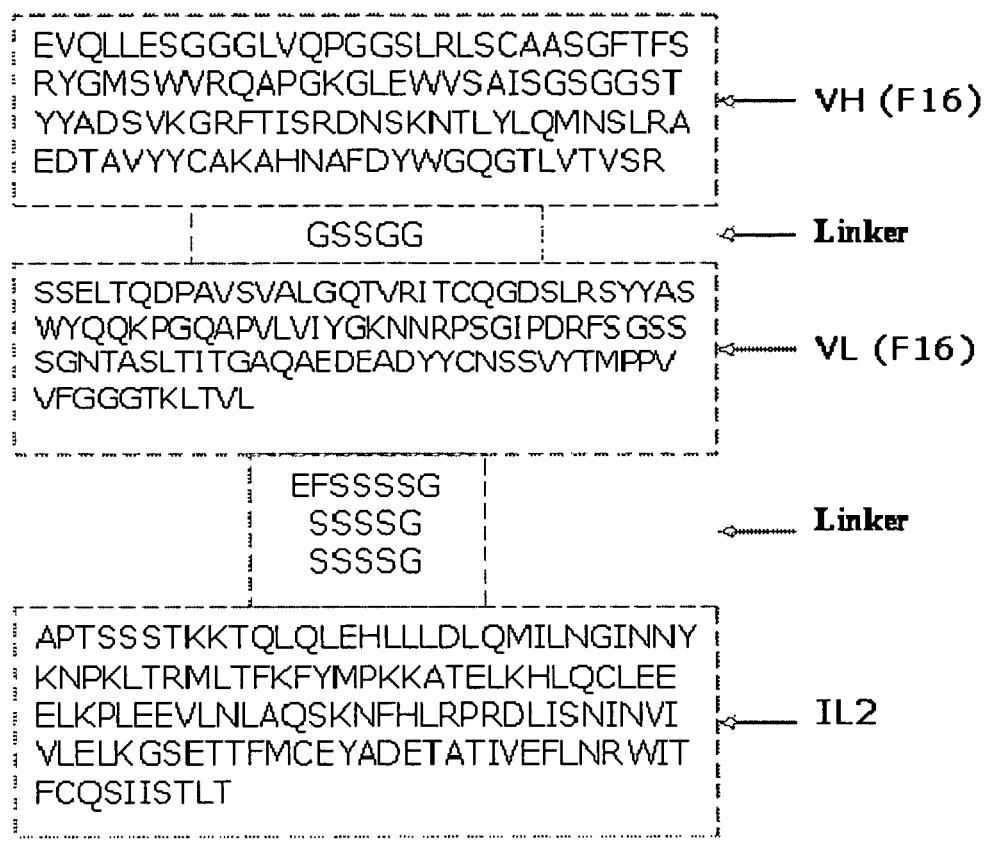
FIG. 6 shows the amino acid sequence SEQ ID NO: 21 of an F16-IL2 immunocytokine, composed of VH(F16) SEQ ID NO: 17, linker SEQ ID NO: 22, VL(F16) SEQ ID NO: 4, linker SEQ ID NO: 20, and IL2 SEQ ID NO: 19.

Measurements of body weights for the four treatment groups confirmed that no weight loss was observed in the control group and in the F16-IL2 treatment group, while temozolomide and the combination of temozolomide+F16-IL2 led to a transient weight loss (with a nadir of 10% and 15% after the fifth injection, respectively). FIG. 5 shows mass of the mice in grams as recorded for the four treatment groups.

Figure 4:
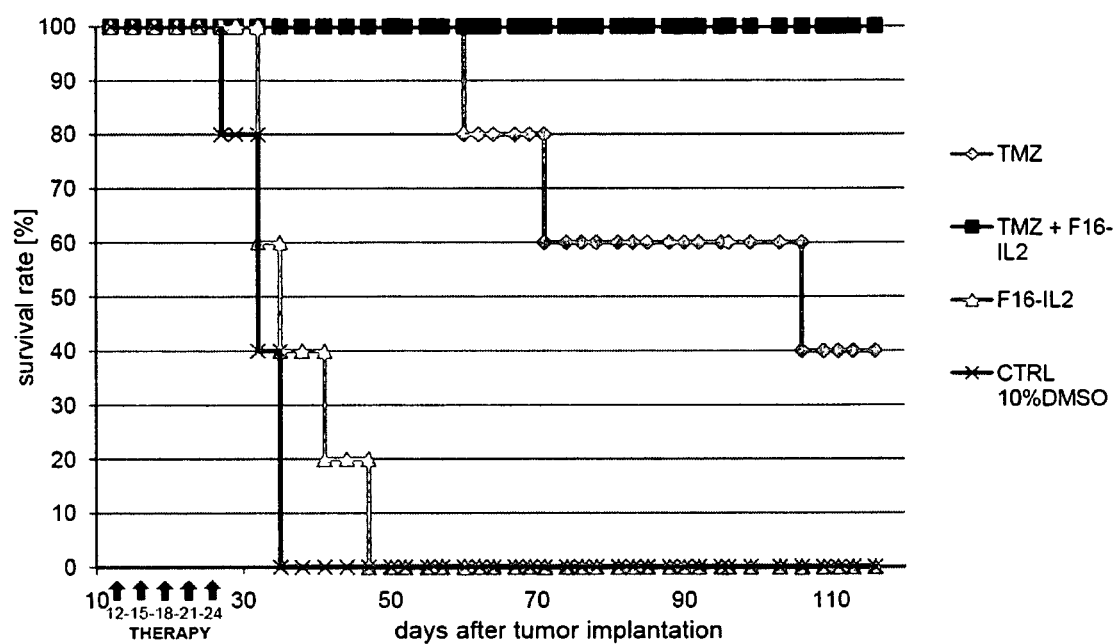
FIG. 4 shows the Kaplan-Meier survival curve of the mice in the experiments with the mouse subcutaneous model of human glioblastoma.

The therapy study with subcutaneous glioblastoma bearing mice disclosed the complete eradication of the tumour in all mice receiving the combined treatment of F16-IL2 and temozolomide. The Kaplan-Meier survival curve is shown in FIG. 4. By day 35, all 10% DMSO-treated control mice were sacrificed because the tumour had approached the cut-off size of 3,000 mm$^3$. The administration of F16-IL2 alone exhibited some therapeutic benefit, with the sacrifice of the last mouse at day 47 from the tumour cell inoculation. Temozolomide alone showed efficacy in determining the survival of two mice over 3 months from the tumour cell injection, but the other animals were sacrificed before day 106 (the tumour had reached the cut-off size). All mice of the combination treatment group (F16-IL2+TMZ) remained alive and tumour-free for over 3 months from the tumour cell injection. One of the five mice in this treatment group had to be sacrificed at day 160 due to weight loss experienced since day 155, but was found to be tumour-free at necropsy.

Analysis of Tumour-Infiltrating Cells and of Microvascular Density in Subcutaneous Glioblastoma Xenografts Human glioblastoma (U87) xenografts were harvested after three injections and sections were analyzed by immunofluorescence. Tumour sections were stained with antibodies anti-asialo GM1, specific for natural killer cells, anti-F4/80, which recognizes macrophages, and anti-CD45, a leukocyte-specific marker.

The largest increase in the infiltration of natural killer cells, macrophages and leukocytes was observed in the F16-IL2 plus temozolomide combination treatment group. The assessment of microvascular density by CD31 staining revealed a general decrease of neo-vessels in the temozolomide-treated groups. Analysis of the F16-IL2 fusion protein within the tumour confirmed the expected localization of the immunocytokine in the perivascular region and in the tumour extracellular matrix.

These results demonstrate the contribution of cytotoxic effector cells to the therapeutic effect of F16-IL2 plus temozolomide combination therapy.

List of Sequences:

```
SEQ ID NO: 1. 4A1-F16 VH domain nucleotide
sequence
GAG GTG CAG CTG TTG GAG TCT GGG GGA GGC TTG GTA

CAG CCT GGG GGG TCC CTG AGA CTC TCC TGT GCA GCC

TCT GGA TTC ACC TTT AGC CGG TAT GGT GCG AGC TGG

GTC CGC CAG GCT CCA GGG AAG GGG CTG GAG TGG GTC

TCA GCT ATT AGT GGT AGT GGT GGT AGC ACA TAC TAC

GCA GAC TCC GTG AAG GGC CGG TTC ACC ATC TCC AGA

GAC AAT TCC AAG AAC ACG CTG TAT CTG CAA ATG AAC

AGC CTG AGA GCC GAG GAC ACG GCC GTA TAT TAC TGT

GCG AAA GCG CAT AAT GCT TTT GAC TAC TGG GGC CAG

GGA ACC CTG GTC ACC GTG TCG AGA

SEQ ID NO: 2 4A1-F16 VH domain amino acid
sequence
EVQLLESGGG LVQPGGSLRL SCAASGFTFS RYGASWVRQA

PGKGLEWVSA ISGSGGSTYY ADSVKGRFTI SRDNSKNTLY

LQMNSLRAED TAVYYCAKAH NAFDYWGQGT LVTVSR

SEQ ID NO: 3 4A1-F16 VL domain nucleotide sequence
TCT TCT GAG CTG ACT CAG GAC CCT GCT GTG TCT GTG

GCC TTG GGA CAG ACA GTC AGG ATC ACA TGC CAA GGA

GAC AGC CTC AGA AGC TAT TAT GCA AGC TGG TAC CAG

CAG AAG CCA GGA CAG GCC CCT GTA CTT GTC ATC TAT

GGT AAA AAC AAC CGG CCC TCA GGG ATC CCA GAC CGA

TTC TCT GGC TCC AGC TCA GGA AAC ACA GCT TCC TTG

ACC ATC ACT GGG GCT CAG GCG GAA GAT GAG GCT GAC

TAT TAC TGT AAC TCC TCT GTT TAT ACT ATG CCG CCC

GTG GTA TTC GGC GGA GGG ACC AAG CTG ACC GTC CTA

SEQ ID NO: 4 4A1-F16 VL domain amino acid sequence
SSELTQDPAVSVALGQTVRITCQGDSLRSYYASWYQQKPGQAPVLVIYGK

NNRPSGIPDRFSGSSSGNTASLTITGAQAEDEADYYCNSSVYTMPPVVFG

GGTKLTVL

SEQ ID NO: 5 4A1-F16 VH CDR1 amino acid sequence:

RYGAS

SEQ ID NO: 6 4A1-F16 VH CDR2 amino acid sequence:

AISGSGGSTYYADSVKG

SEQ ID NO: 7 4A1-F16 VH CDR3 amino acid sequence:

AHNAFDY

SEQ ID NO: 8 4A1-F16 VL CDR1 amino acid sequence:

QGDSLRSYYAS

SEQ ID NO: 9 4A1-F16 VL CDR2 amino acid sequence:

GKNNRPS

SEQ ID NO: 10 4A1-F16 VL CDR3 amino acid sequence:

NSSVYTMPPVV

SEQ ID NO: 11 hIL2 precursor sequence
MYRMQLLSCI ALSLALVTNS APTSSSTKKT QLQLEHLLLD

LQMILNGINN YKNPKLTRML TFKFYMPKKA TELKHLQCLE

EELKPLEEVL NLAQSKNFHL RPRDLISNIN VIVLELKGSE

TTFMCEYADE TATIVEFLNR WITFCQSIIS TLT

SEQ ID NO: 12 Peptide linker amino acid sequence:

GGGGSGGGGSGGGG

SEQ ID NO: 13 Peptide linker amino acid sequence:

GGGGSGGGGSGGGGS
```

-continued
SEQ ID NO: 14 Peptide linker amino acid sequence:
SSSSGSSSSGSSSSG

SEQ ID NO: 15 Peptide linker amino acid sequence:
GSGSAGSGSAGSGSA

SEQ ID NO: 16 Peptide linker amino acid sequence:
GGSGGGGSGGGGSGG

SEQ ID NO: 17 Improved F16 VH domain amino acid
sequence
EVQLLESGGG LVQPGGSLRL SCAASGFTFS RYGMSWVRQA

PGKGLEWVSA ISGSGGSTYY ADSVKGRFTI SRDNSKNTLY

LQMNSLRAED TAVYYCAKAH NAFDYWGQGT LVTVSR

SEQ ID NO: 18 Improved F16 VH CDR1 amino acid sequence: RYGMS

SEQ ID NO: 19 Human IL-2 amino acid sequence-
mature sequence
APTSSSTKKT QLQLEHLLLD LQMILNGINN YKNPKLTRML

TFKFYMPKKA TELKHLQCLE EELKPLEEVL NLAQSKNFHL

RPRDLISNIN VIVLELKGSE TTFMCEYADE TATIVEFLNR

WITFCQSIIS TLT

SEQ ID NO: 20 Peptide linker amino acid sequence
EFSSSSGSSSSGSSSSG

SEQ ID NO: 21 F16-IL2 Immunocytokine amino acid
sequence
EVQLLESGGG LVQPGGSLRL SCAASGFTFS RYGMSWVRQA

PGKGLEWVSA ISGSGGSTYY ADSVKGRFTI SRDNSKNTLY

LQMNSLRAED TAVYYCAKAH NAFDYWGQGT LVTVSRGSSG

GSSELTQDPA VSVALGQTVR ITCQGDSLRS YYASWYQQKP

GQAPVLVIYG KNNRPSGIPD RFSGSSSGNT ASLTITGAQA

EDEADYYCNS SVYTMPPVVF GGGTKLTVLE FSSSSGSSSS

GSSSSGAPTS SSTKKTQLQL EHLLLDLQMI LNGINNYKNP

KLTRMLTFKF YMPKKATELK HLQCLEEELK PLEEVLNLAQ

SKNFHLRPRD LISNINVIVL ELKGSETTFM CEYADETATI

VEFLNRWITF CQSIISTLT

SEQ ID NO: 22 Peptide linker amino acid sequence:
GSSGG

SEQ ID NO: 23 Improved F16 VH domain nucleotide
sequence
GAG GTG CAG CTG TTG GAG TCT GGG GGA GGC TTG GTA

CAG CCT GGG GGG TCC CTG AGA CTC TCC TGT GCA GCC

TCT GGA TTC ACC TTT AGC CGG TAT GGT ATG AGC TGG

GTC CGC CAG GCT CCA GGG AAG GGG CTG GAG TGG GTC

TCA GCT ATT AGT GGT AGT GGT GGT AGC ACA TAC TAC

GCA GAC TCC GTG AAG GGC CGG TTC ACC ATC TCC AGA

GAC AAT TCC AAG AAC ACG CTG TAT CTG CAA ATG AAC

AGC CTG AGA GCC GAG GAC ACG GCC GTA TAT TAC TGT

GCG AAA GCG CAT AAT GCT TTT GAC TAC TGG GGC CAG

GGA ACC CTG GTC ACC GTG TCG AGA

References

1 Bosslet Cancer Res. 1998
2 Adams G P, Weiner L M. Nat Biotechnol. 23:1147-1157 2005
3 Carter P J. Nat Rev Immunol. 6:343-357 2006
4 Schrama D, Reisfeld R A, Becker J C. Nat Rev Drug Discov. 5:147-159 2006
5 Neri D, Bicknell R. Nat Rev Cancer. 5:436-446 2005
6 Thorpe P E. Clin Cancer Res. 10:415-427 2004
7 Schliemann C, Neri D. Biochim Biophys Acta. 1776:175-192 2007
8 Riva P et al. *Int J Cancer,* 51:7-13 1992
9 Riva P et al. *Cancer Res* 55:5952s-5956s 1995
10 Paganelli G et al *Eur J Nucl Med* 21:314-321 1994
11 Reardon D A et al. *J Clin Oncol* 20:1389-1397 2002
12 Bigner D D et al. *J Clin Oncol* 16:2202-2212 1998
13 Halin, C, et al. Nat Biotechnol. 20:264-269 2002
14 Carnemolla B, et al. Blood. 99:1659-1665 2002
15 Borsi L, et al. Blood. 102:4384-4392 2003
16 Ebbinghaus C, et al. Int J Cancer. 116:304-313 2005
17 Kaspar M, Trachsel E, Neri D. Cancer Res. 67:4940-4948 2007
18 Tijink B M et al., J Nucl Med. 47:1127-1135 2006
19 Birchler et al. Nat Biotechnol. 17:984-988 1999
20 Halin, C, et al. Cancer Res. 63:3202-3210 2003
21 Menrad A, Menssen H D. 9:491-500 2005
22 Mårlind et al. *Clin Cancer Res.* 14(20):6515-6524 2008
23 Viti, F., et al., Cancer Res, 1999. 59(2): p. 347-52
24 Nilsson, F., et al., Cancer Res, 2001. 61(2): p. 711-6
25 Brack et al. *Clin Cancer Res;* 12:3200-8 2006
26 Burnet N G et al *Br J Cancer* 92:241-245 2005
27 CBTRUS, Statistical Reports: Primary Brain Tumours in the United States: 1995-1999 and 1997-2000
28 Ferlay J et al: Globocan 2000: Cancer incidence, mortality and prevalence worldwide. IARC Press, Lyon 2000
29 Castellani I J C 1994
30 Castellani P et al. American Journal of Pathology; 161: 1695-1700 2002
31 Santimaria, 2003, Clin Cancer Res
32 Leins et al. *Cancer* 98(11):2430-2439 2003
33 Bartolomei et al. Q *J Nucl Med* 48:220-228 2004
34 Darkes et al. *Am. J. Cancer* 1(1):55-90 2002
35 Kleihues P, Cavenee W K: WHO, Pathology & Genetics, Tumours of the Nervous System. IARC Press, Lyon 2000
36 Ohgaki H et al. *Cancer Res* 64, 6892-6899 2004
37 Schliemann et al. *Blood* November 2008
38 Dunne J et al. J Immunol.; 167:3129-3138 2001
39 Albertsson P A et al., Trends Immunol.; 24:603-609 2003
40 Altschul et al. *J. Mol. Biol.* 215: 405-410 1990
41 Pearson and Lipman *PNAS USA* 85: 2444-2448 1988
42 Smith and Waterman *J. Mol Biol.* 147: 195-197 1981
43 Nucl. Acids Res. 25 3389-3402 1997
44 Stupp et al *The New England Journal of Medicine,* 352: 987-96 2005
45 Holliger & Hudson, *Nature Biotechnology* 23(9):1126-1136 2005
46 Ward, E. S. et al., Nature 341, 544-546 (1989)
47 McCafferty et al (1990) Nature, 348, 552-554
48 Holt et al (2003) Trends in Biotechnology 21, 484-490
49 Bird et al, Science, 242, 423-426, 1988

50 Huston et al, PNAS USA, 85, 5879-5883, 1988
51 Holliger, P. et al, Proc. Natl. Acad. Sci. USA 90 6444-6448, 1993
52 Reiter, Y. et al, Nature Biotech, 14, 1239-1245, 1996
53 Hu, S. et al, Cancer Res., 56, 3055-3061, 1996
54 Qui et al., *Nat. Biotechnol.* 25:921-929 2007
55 Holliger and Bohlen 1999 Cancer and metastasis rev. 18: 411-419
56 Holliger, P. and Winter G. Current Opinion Biotechnol 4, 446-449 1993
57 Glennie M J et al., 1987 J. Immunol. 139, 2367-2375
58 Repp R. et al., 1995 J. Hemat. 377-382
59 Staerz U. D. and Bevan M. J. 1986 PNAS 83
60 Suresh M. R. et al., 1986 Method Enzymol. 121: 210-228
61 Merchand et al., 1998 Nature Biotech. 16:677-681
62 Ridgeway, J. B. B. et al, Protein Eng., 9, 616-621, 1996
63 Harlow and Lane, Antibodies: A Laboratory Manual, Cold Spring Harbor Laboratory, Cold Spring Harbor N.Y., pp. 726, 1988
64 Köhler and Milstein, Nature, 256:495-497, 1975
65 Borsi L et al. Int J Cancer; 102:75-85 2002
66 Bello et a Clinical Cancer Research, 10: 4527-37 2004
67 Friedman et al. Clinical Cancer Research 6: 2585-97 2000

The invention claimed is:

1. A method of treating glioblastoma in an individual, comprising administering a chemotherapeutic agent and an immunocytokine to the individual, wherein the chemotherapeutic agent is temozolomide and wherein the immunocytokine comprises interleukin-2 (IL2) conjugated to an antibody molecule that binds domain A1 of tenasin-C large isoform, wherein the antibody molecule comprises an antibody-antigen binding site comprising a VH domain and a VL domain, the VH domain comprising:
a VH CDR1 of SEQ ID NO: 18 or a VH CDR1 of SEQ ID NO:5;
a VH CDR2 of SEQ ID NO: 6;
and a VH CDR3 of SEQ ID NO: 7;
and the VL domain comprising:
a VL CDR1 of SEQ ID NO:8;
a VL CDR2 of SEQ ID NO:9; and a VL CDR3 of SEQ ID NO:10.

2. A method according to claim 1 wherein the antibody molecule comprises an antibody-antigen binding site comprising the 4A1-F16 VH domain SEQ ID NO. 17 and the 4A1-F16 VL domain SEQ ID NO:4.

3. A method according to claim 1, wherein the antibody molecule comprises an antibody-antigen binding site comprising the 4A1-F16 VH domain SEQ ID NO:2 and the 4A1-F16 VH domain SEC ID NO:4.

4. A method according to claim 1, wherein the immunocytokine comprises IL2 conjugated to an scFv antibody molecule.

5. A method according to claim 1, wherein treating the glioblastoma comprises retarding growth of the glioblastoma, reducing size of the glioblastoma or inhibiting regrowth of the glioblastoma in the individual.

6. A method according to claim 2, wherein the immunocytokine comprises IL2 conjugated to an scFv antibody molecule.

7. A method according to claim 3, wherein the immunocytokine comprises IL2 conjugated to an scFv antibody molecule.

8. A pharmaceutical composition for the treatment of glioblastoma comprising effective amounts of temozolomide and interleukin 2 conjugated to an antibody molecule that binds domain A1 of tenascin-C isoform, wherein the antibody molecule comprises an antibody-antigen binding site comprising a VH domain and a VL domain, the VH domain comprising:
a VH CDR1 of SEQ ID NO: 18 or a VH CDR1 of SEQ ID NO:5;
a VH CDR2 of SEQ ID NO: 6;
and a VH CDR3 of SEQ ID NO: 7;
and the VL domain comprising:
a VL CDR1 of SEQ ID NO: 8;
a VL CDR2 of SEQ ID NO:9; and a VL CDR3 of SEQ ID NO:10 in a pharmaceutically acceptable carrier.

9. The pharmaceutical composition of claim 8 wherein the immunocytokine comprises IL2 conjugated to an scFv antibody molecule.

10. The method of claim 1, comprising administering the immunocytokine Lathe individual by intravenous injection.

11. The pharmaceutical composition of claim 8, wherein the composition is formulated for intravenous injection of the interleukin 2 conjugated to the antibody molecule.

12. The pharmaceutical composition of claim 11, wherein the composition is formulated for separate administration of the temozolomide and the antibody molecule.

* * * * *

SEQUENCE LISTING

```
<160> NUMBER OF SEQ ID NOS: 27

<210> SEQ ID NO 1
<211> LENGTH: 348
<212> TYPE: DNA
<213> ORGANISM: Homo sapiens

<400> SEQUENCE: 1
gaggtgcagc tgttggagtc tgggggaggc ttggtacagc ctgggggtc  cctgagactc      60 tcctgtgcag cctctggatt caccttagc cggtatggtg cgagctgggt ccgccaggct     120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtat attactgtgc gaaagcgcat    300
aatgcttttg actactgggg ccagggaacc ctggtcaccg tgtcgaga                 348

<210> SEQ ID NO 2
<211> LENGTH: 116
<212> TYPE: PRT
<213> ORGANISM: Homo sapiens

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Ala Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala His Asn Ala Phe Asp Tyr Trp Gly Gln Gly Thr Leu Val
            100                 105                 110

Thr Val Ser Arg
        115

<210> SEQ ID NO 3
<211> LENGTH: 324
<212> TYPE: DNA
<213> ORGANISM: Homo sapiens

<400> SEQUENCE: 3
```

```
tcttctgagc tgactcagga ccctgctgtg tctgtggcct tgggacagac agtcaggatc      60
acatgccaag agacagcct  cagaagctat tatgcaagct ggtaccagca gaagccagga     120
caggcccctg tacttgtcat ctatggtaaa acaaccggc  cctcagggat cccagaccga     180
ttctctggct ccagctcagg aaacacagct tccttgacca tcactggggc tcaggcggaa     240
gatgaggctg actattactg taactcctct gtttatacta tgccgcccgt ggtattcggc     300
ggagggacca agctgaccgt ccta                                            324
```

<210> SEQ ID NO 4
<211> LENGTH: 108
<212> TYPE: PRT
<213> ORGANISM: Homo sapiens

<400> SEQUENCE: 4

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser Val Tyr Thr Met Pro Pro
                85                  90                  95

Val Val Phe Gly Gly Gly Thr Lys Leu Thr Val Leu
            100                 105

<210> SEQ ID NO 5
<211> LENGTH: 5
<212> TYPE: PRT
<213> ORGANISM: Homo sapiens

<400> SEQUENCE: 5

Arg Tyr Gly Ala Ser
1               5

<210> SEQ ID NO 6
<211> LENGTH: 17
<212> TYPE: PRT
<213> ORGANISM: Homo sapiens

<400> SEQUENCE: 6

Ala Ile Ser Gly Ser Gly Gly Ser Thr Tyr Tyr Ala Asp Ser Val Lys
1               5                   10                  15

Gly

<210> SEQ ID NO 7
<211> LENGTH: 7
<212> TYPE: PRT
<213> ORGANISM: Homo sapiens

<400> SEQUENCE: 7

Ala His Asn Ala Phe Asp Tyr
1               5

<210> SEQ ID NO 8
<211> LENGTH: 11
<212> TYPE: PRT

```
<213> ORGANISM: Homo sapiens

<400> SEQUENCE: 8

Gln Gly Asp Ser Leu Arg Ser Tyr Tyr Ala Ser
1               5                   10

<210> SEQ ID NO 9
<211> LENGTH: 7
<212> TYPE: PRT
<213> ORGANISM: Homo sapiens

<400> SEQUENCE: 9

Gly Lys Asn Asn Arg Pro Ser
1               5

<210> SEQ ID NO 10
<211> LENGTH: 11
<212> TYPE: PRT
<213> ORGANISM: Homo sapiens

<400> SEQUENCE: 10

Asn Ser Ser Val Tyr Thr Met Pro Pro Val Val
1               5                   10

<210> SEQ ID NO 11
<211> LENGTH: 153
<212> TYPE: PRT
<213> ORGANISM: Homo sapiens

<400> SEQUENCE: 11

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
        50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 12
<211> LENGTH: 14
<212> TYPE: PRT
<213> ORGANISM: Artificial sequence
<220> FEATURE:
<223> OTHER INFORMATION: Synthetic sequence: Peptide linker amino acid
      sequence

<400> SEQUENCE: 12

Gly Gly Gly Gly Ser Gly Gly Gly Ser Gly Gly Gly Gly
1               5                   10
```

```
<210> SEQ ID NO 13
<211> LENGTH: 15
<212> TYPE: PRT
<213> ORGANISM: Artificial sequence
<220> FEATURE:
<223> OTHER INFORMATION: Synthetic sequence: Peptide linker amino acid
      sequence

<400> SEQUENCE: 13

Gly Gly Gly Gly Ser Gly Gly Gly Gly Ser Gly Gly Gly Gly Ser
1               5                   10                  15

<210> SEQ ID NO 14
<211> LENGTH: 15
<212> TYPE: PRT
<213> ORGANISM: Artificial sequence
<220> FEATURE:
<223> OTHER INFORMATION: Synthetic sequence: Peptide linker amino acid
      sequence

<400> SEQUENCE: 14

Ser Ser Ser Ser Gly Ser Ser Ser Ser Gly Ser Ser Ser Ser Gly
1               5                   10                  15

<210> SEQ ID NO 15
<211> LENGTH: 15
<212> TYPE: PRT
<213> ORGANISM: Artificial sequence
<220> FEATURE:
<223> OTHER INFORMATION: Synthetic sequence: Peptide linker amino acid
      sequence

<400> SEQUENCE: 15

Gly Ser Gly Ser Ala Gly Ser Gly Ser Ala Gly Ser Gly Ser Ala
1               5                   10                  15

<210> SEQ ID NO 16
<211> LENGTH: 15
<212> TYPE: PRT
<213> ORGANISM: Artificial sequence
<220> FEATURE:
<223> OTHER INFORMATION: Synthetic sequence: Peptide linker amino acid
      sequence

<400> SEQUENCE: 16

Gly Gly Ser Gly Gly Gly Ser Gly Gly Gly Ser Gly Gly
1               5                   10                  15

<210> SEQ ID NO 17
<211> LENGTH: 116
<212> TYPE: PRT
<213> ORGANISM: Artificial sequence
<220> FEATURE:
<223> OTHER INFORMATION: Synthetic sequence: Improved F16 VH domain
      amino acid sequence

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Lys Ala His Asn Ala Phe Asp Tyr Trp Gly Gln Gly Thr Leu Val
        100                 105                 110

Thr Val Ser Arg
        115

<210> SEQ ID NO 18
<211> LENGTH: 5
<212> TYPE: PRT
<213> ORGANISM: Artificial sequence
<220> FEATURE:
<223> OTHER INFORMATION: Synthetic sequence: Improved F16 VH CDR1 domain
      amino acid sequence

<400> SEQUENCE: 18

Arg Tyr Gly Met Ser
1               5

<210> SEQ ID NO 19
<211> LENGTH: 133
<212> TYPE: PRT
<213> ORGANISM: Homo sapiens

<400> SEQUENCE: 19

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
             20                  25                  30

Asn Pro Lys Leu Thr Arg Met Leu Thr Phe Lys Phe Tyr Met Pro Lys
         35                  40                  45

Lys Ala Thr Glu Leu Lys His Leu Gln Cys Leu Glu Glu Glu Leu Lys
     50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
             85                  90                  95

Lys Gly Ser Glu Thr Thr Phe Met Cys Glu Tyr Ala Asp Glu Thr Ala
        100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 20
<211> LENGTH: 17
<212> TYPE: PRT
<213> ORGANISM: Artificial sequence
<220> FEATURE:
<223> OTHER INFORMATION: Synthetic sequence: Peptide linker amino acid
      sequence

<400> SEQUENCE: 20

Glu Phe Ser Ser Ser Ser Gly Ser Ser Ser Gly Ser Ser Ser
1               5                   10                  15

Gly

<210> SEQ ID NO 21
<211> LENGTH: 379
```

<212> TYPE: PRT
<213> ORGANISM: Artificial sequence
<220> FEATURE:
<223> OTHER INFORMATION: Synthetic sequence: F16-IL2 Immunocytokine amino acid sequence

<400> SEQUENCE: 21

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala His Asn Ala Phe Asp Tyr Trp Gly Gln Gly Thr Leu Val
            100                 105                 110

Thr Val Ser Arg Gly Ser Ser Gly Gly Ser Ser Glu Leu Thr Gln Asp
        115                 120                 125

Pro Ala Val Ser Val Ala Leu Gly Gln Thr Val Arg Ile Thr Cys Gln
    130                 135                 140

Gly Asp Ser Leu Arg Ser Tyr Tyr Ala Ser Trp Tyr Gln Gln Lys Pro
145                 150                 155                 160

Gly Gln Ala Pro Val Leu Val Ile Tyr Gly Lys Asn Asn Arg Pro Ser
                165                 170                 175

Gly Ile Pro Asp Arg Phe Ser Gly Ser Ser Ser Gly Asn Thr Ala Ser
            180                 185                 190

Leu Thr Ile Thr Gly Ala Gln Ala Glu Asp Glu Ala Asp Tyr Tyr Cys
        195                 200                 205

Asn Ser Ser Val Tyr Thr Met Pro Pro Val Val Phe Gly Gly Gly Thr
    210                 215                 220

Lys Leu Thr Val Leu Glu Phe Ser Ser Ser Ser Gly Ser Ser Ser Ser
225                 230                 235                 240

Gly Ser Ser Ser Ser Gly Ala Pro Thr Ser Ser Thr Lys Lys Thr
                245                 250                 255

Gln Leu Gln Leu Glu His Leu Leu Leu Asp Leu Gln Met Ile Leu Asn
            260                 265                 270

Gly Ile Asn Asn Tyr Lys Asn Pro Lys Leu Thr Arg Met Leu Thr Phe
        275                 280                 285

Lys Phe Tyr Met Pro Lys Lys Ala Thr Glu Leu Lys His Leu Gln Cys
    290                 295                 300

Leu Glu Glu Glu Leu Lys Pro Leu Glu Glu Val Leu Asn Leu Ala Gln
305                 310                 315                 320

Ser Lys Asn Phe His Leu Arg Pro Arg Asp Leu Ile Ser Asn Ile Asn
                325                 330                 335

Val Ile Val Leu Glu Leu Lys Gly Ser Glu Thr Thr Phe Met Cys Glu
            340                 345                 350

Tyr Ala Asp Glu Thr Ala Thr Ile Val Glu Phe Leu Asn Arg Trp Ile
        355                 360                 365

Thr Phe Cys Gln Ser Ile Ile Ser Thr Leu Thr
    370                 375
```

```
<210> SEQ ID NO 22
<211> LENGTH: 5
<212> TYPE: PRT
<213> ORGANISM: Artificial sequence
<220> FEATURE:
<223> OTHER INFORMATION: Synthetic sequence: Peptide linker amino acid
      sequence

<400> SEQUENCE: 22

Gly Ser Ser Gly Gly
1               5

<210> SEQ ID NO 23
<211> LENGTH: 348
<212> TYPE: DNA
<213> ORGANISM: Artificial sequence
<220> FEATURE:
<223> OTHER INFORMATION: Synthetic sequence: Improved F16 VH domain
      nucleotide sequence

<400> SEQUENCE: 23
gaggtgcagc tgttggagtc tgggggaggc ttggtacagc ctgggggtc cctgagactc      60 tcctgtgcag cctctggatt cacctttagc cggtatggta tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtat attactgtgc gaaagcgcat    300
aatgcttttg actactgggg ccagggaacc ctggtcaccg tgtcgaga                 348

<210> SEQ ID NO 24
<211> LENGTH: 5
<212> TYPE: PRT
<213> ORGANISM: Artificial sequence
<220> FEATURE:
<223> OTHER INFORMATION: Synthetic sequence: Linker motif

<400> SEQUENCE: 24

Gly Gly Gly Gly Ser
1               5

<210> SEQ ID NO 25
<211> LENGTH: 5
<212> TYPE: PRT
<213> ORGANISM: Artificial sequence
<220> FEATURE:
<223> OTHER INFORMATION: Synthetic sequence: Linker motif

<400> SEQUENCE: 25

Ser Ser Ser Ser Gly
1               5

<210> SEQ ID NO 26
<211> LENGTH: 5
<212> TYPE: PRT
<213> ORGANISM: Artificial sequence
<220> FEATURE:
<223> OTHER INFORMATION: Synthetic sequence: Linker motif

<400> SEQUENCE: 26

Gly Ser Gly Ser Ala
1               5

<210> SEQ ID NO 27
<211> LENGTH: 5
<212> TYPE: PRT
```

-continued

```
<213> ORGANISM: Artificial sequence
<220> FEATURE:
<223> OTHER INFORMATION: Synthetic sequence: Linker motif

<400> SEQUENCE: 27

Gly Gly Ser Gly Gly
1               5
```